United States Patent [19]

Yoshida et al.

[11] Patent Number: 4,589,414
[45] Date of Patent: May 20, 1986

[54] SURGICAL CUTTING INSTRUMENT

[75] Inventors: Yutaka Yoshida; Shozo Hirayama, both of Hachioji; Hiroyuki Kusunoki, Higashimurayama; Yoshio Shishido, Sagamihara; Kazumasa Matsuo, Tama; Morihide Mizumoto, Hachioji; Masahiko Kato, Akikawa; Tadao Hagino, Yokohama, all of Japan

[73] Assignee: Olympus Optical Co., Ltd., Japan

[21] Appl. No.: 602,607

[22] Filed: Apr. 20, 1984

[30] Foreign Application Priority Data

Apr. 27, 1983 [JP] Japan .................... 58-74762

[51] Int. Cl.⁴ .................. A61F 17/32; A61B 17/20
[52] U.S. Cl. ........................... 128/305; 604/22
[58] Field of Search .............. 604/22; 128/305, 312; 30/240

[56] References Cited

U.S. PATENT DOCUMENTS

| | | | |
|---|---|---|---|
| 2,894,324 | 7/1959 | Hardin | 30/240 |
| 3,815,604 | 6/1974 | O'Malley et al. | 604/22 |
| 3,995,619 | 12/1976 | Glatzer | 128/305 |
| 4,137,920 | 2/1979 | Bonnet | 128/305 |
| 4,210,146 | 7/1980 | Banko | 128/305 |
| 4,461,281 | 7/1984 | Carson | 128/305 |

Primary Examiner—C. Fred Rosenbaum
Assistant Examiner—Gene B. Kartchner
Attorney, Agent, or Firm—Ostrolenk, Faber, Gerb & Soffen

[57] ABSTRACT

A surgical cutting instrument essentially comprises an outer sheath tube, an inner stationary tube which is disposed within said outer sheath tube such that the distal end of the inner tube projects from the distal end of the outer sheath tube and is provided with a cutting opening for drawing cut tissue chips at the peripheral wall of the distal end of the inner tube and a sliding member which is slidably disposed between said outer sheath tube and said inner tube so as to open and close said cutting opening and is provided with an outer cutting edge which engages an inner cutting edge of said cutting opening, on the distal end edge of the sliding member, whereby a body tissue is cut by axially and slidingly reciprocating said sliding member to open and close said cutting opening and cut tissue chips are withdrawn from the body by suction through a suction channel of the inner tube.

10 Claims, 8 Drawing Figures

SURGICAL CUTTING INSTRUMENT

BACKGROUND OF THE INVENTION

The present invention relates to a surgical cutting instrument, and more particularly, to a surgical cutting instrument capable of, while being inserted into a body cavity, particularly a joint cavity of the knee, for example, performing a easy and reliable cutting and evacuating operation of a cartilage, bone, fibrous tissue, tumor or the like.

A conventional operation of a joint generally employs an incision method (open surgery). By way of example, a commonly used operation of the knee such as to remove a tumor on the patella or to excise a damaged cartilage or a bone from the knee joint requires a large incision of an epithelium. Consequently, the operation is attended with a trauma by the incision. Thus, the trauma will cause pain and limitations of movement. Furthermore, a considerable time is required for recovery from the trauma.

Accordingly, there has recently been proposed an instrument in which under observation with an arthroscope (endoscope) a small perforation is provided on an epithelium without incising the knee epithelium and an operation is effected inserting a probe into the perforation (closed surgery). For instance, such instruments are disclosed in U.S. Pat. No. 4,203,444 and U.S. Pat. No. 4,246,902.

The prior art instrument disclosed in U.S. Pat. No. 4,203,444 comprises an elongate external stationary tube defining a side-facing, axially extending shaving port on the periphery of the external tube, an internal tube which is rotatably mounted within the external tube and defines an internal, rotary blade at the shaving port, a suction apparatus and a drive motor. The instrument severs tissue or the like by rotating the rotary blade with the drive motor and draws shavings by suction to remove them through the internal member.

With the conventional instrument of the above construction, since in the shaving port, an outer cutting edge is formed on the inner periphery of the external tube and the rotary blade forms an inner cutting edge, it is difficult to take steady aim at a tissue to be cut and a bite between the outer and the inner cutting edges is not good. In addition, since the cutting operation is effected only after a tissue to be cut is drawn in the shaving port of the external tube by means of the suction apparatus, it is difficult to cut a tissue such as a cartilage or a bone. To rotate the internal tube forming a suction channel therein, a rotary shaft passes through the suction channel and therefore cut or shaved tissue is not smoothly sucked and withdrawn.

The prior art instrument disclosed in U.S. Pat. No. 4,246,902 comprises a probe-like outer, elongate member having a distal end with a cutting aperture in a side wall thereof, an inner cutting member which is slidably disposed within the outer member and has a distal end defining a cutting edge positioned at said distal end of the outer member, a suction apparatus and a drive mechanism for the inner cutting member. The instrument cuts a tissue to be cut which is drawn by suction in the cutting aperture by reciprocation of the inner cutting member and then the cut tissue is sucked and evacuated. The instrument thus constructed, however, has disadvantages as indicated in the former prior art, also. Specifically, since the inner cutting member which is disposed within the outer member forms an inner cutting edge, it is difficult to take steady aim at a tissue to be cut and a bite between the outer member and the inner cutting edge is not good. In addition, it is difficult to cut a comparatively hard tissue such as a cartilage or bone. Since the inner cutting member is slidably disposed within a suction channel passage, cut tissue is not smoothly sucked and withdrawn.

SUMMARY OF THE INVENTION

It is an object of the invention to provide a surgical cutting instrument which comprises an outer sheath tube having an open distal end, an inner stationary tube which is disposed within the outer sheath tube in such a manner that a closed distal end of the inner tube projects from the open distal end of the outer tube, a cutting opening for drawing tissue chips which is provided on the peripheral wall of the projected distal end portion of the inner tube to form an inner cutting edge at the edge of the cutting opening, a suction passage for cut tissue chips which is provided within the inner stationary tube acting as a suction tube and communicating with the cutting opening, and a sliding member which is disposed between the inner periphery of the outer tube and the outer periphery of the inner stationary tube so as to be slidable in the axial direction and to close and open the cutting opening of the inner stationary tube and which is provided with an outer cutting edge which engages the inner cutting edge at the distal end of the sliding member.

According to the invention, the arrangement in which the inner cutting edge is formed at the edge of the cutting opening on the outer periphery of the inner stationary tube and the outer cutting edge is formed on the sliding member which reciprocates on the outer periphery of the inner stationary tube makes it easy to take accurate aim at a tissue to be cut or shaved and to improve the bite of the tissue between the outer and the inner cutting edges so that escape of the tissue is avoided. Thus, the cutting and shaving operation can be assured.

Since no other member such as a rotary shaft passes through the suction passage and the suction passage body itself does not reciprocate or rotate, cut or shaved tissue chips can be smoothly sucked and evacuated.

In addition, since the cutting opening for drawing tissue is provided at an easily visible position on the distal end of the instrument, it is possible to easily take accurate aim at a tissue to be removed. Thus, the cutting operation is reliably limited to merely the affected tissue to be cut or shaved.

DESCRIPTION OF A PREFERRED EMBODIMENT

Figure 1:
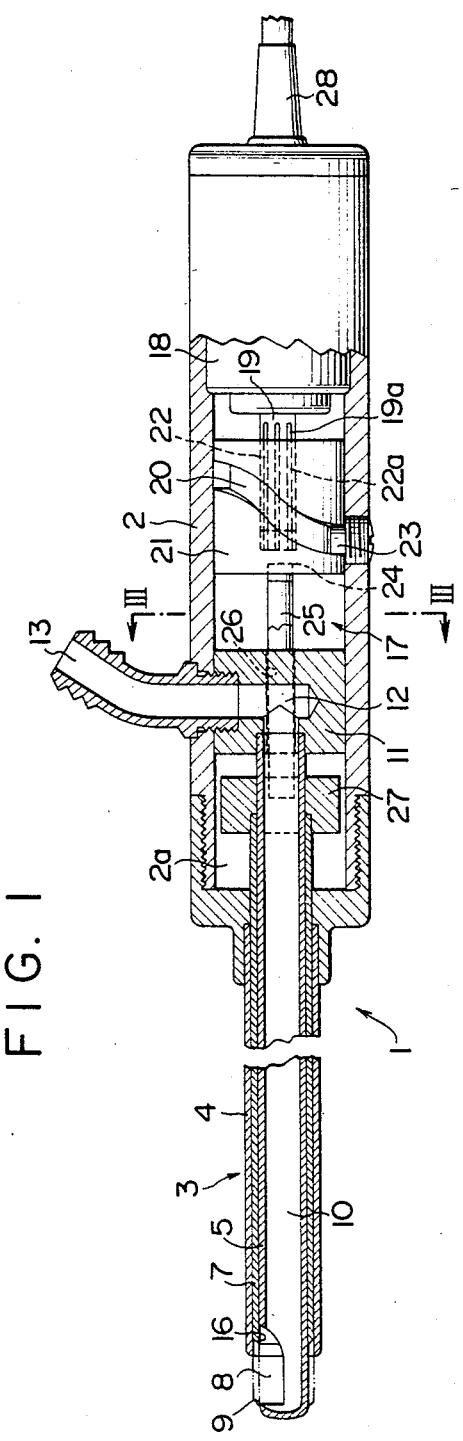
FIG. 1 is a cross-sectional view of essential parts of one embodiment of a surgical cutting instrument according to the invention.

Referring now to FIG. 1, a surgical cutting instrument 1 according to one embodiment of the invention comprises a grip 2 at its proximal side and an elongate inserter 3 forwardly extending from the grip 2 (left in FIG. 1) and is inserted into a body cavity, particularly the joint cavity. The inserter 3 comprises an outer sheath tube 4 which has its open distal and proximal ends, the latter of which ends is secured to the distal end of the grip 2, an inner stationary tube 5 which is disposed within the outer sheath tube 4 such that a closed distal end of the inner tube 5 projects from the open distal end of the outer sheath tube 4 and a sliding member 7 which is in a close sliding fit between the inner periphery of the outer sheath tube 4 and the outer periphery of the inner tube 5 so as to be axially slidable.

Figure 2D:
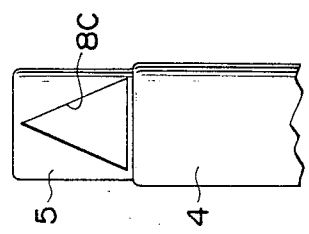
FIGS. 2(A) to 2(D) are enlarged plan views of essential parts of respective examples of cutting openings for withdrawing tissue in the surgical cutting instrument shown in FIG. 1.
Figure 2C:
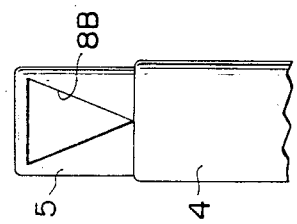
Figure 2B:
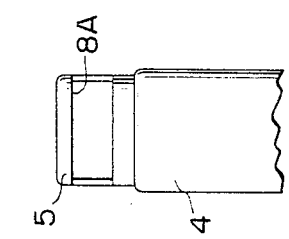
Figure 2A:
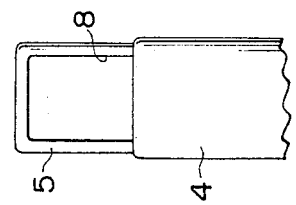
Figure 5:
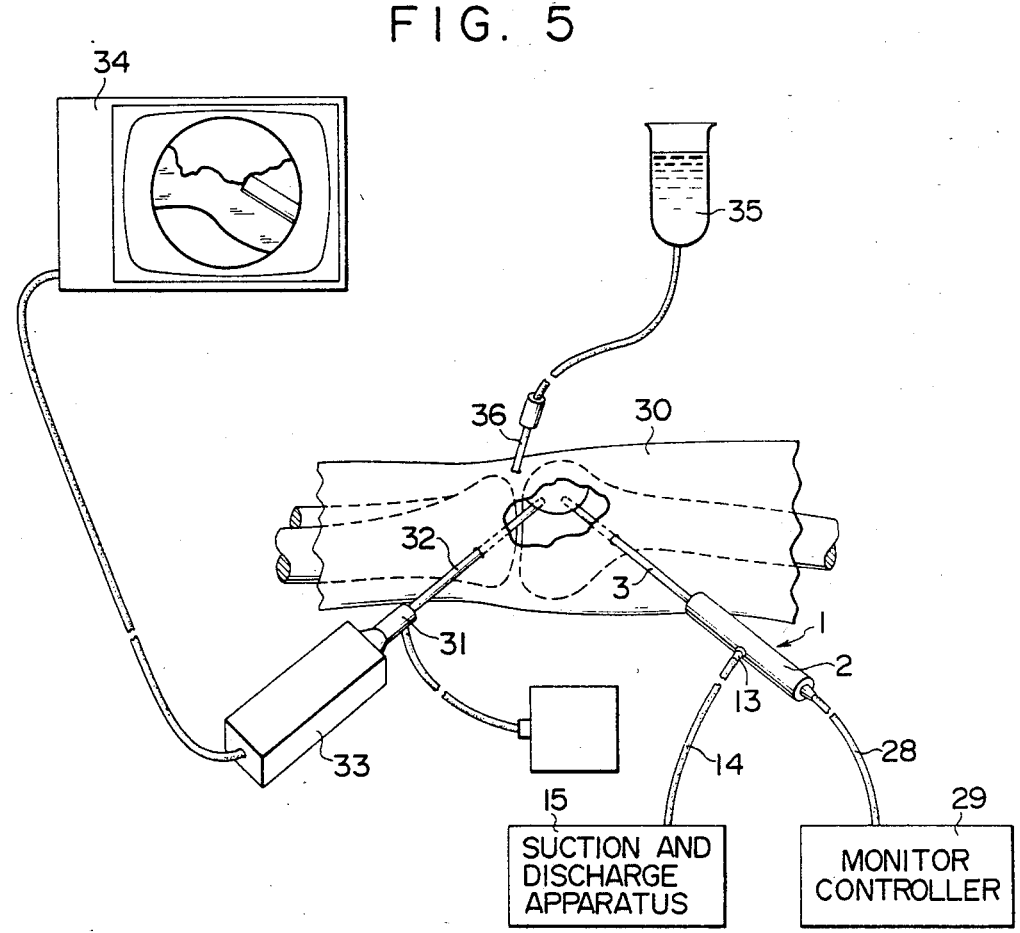
FIG. 5 is a schematic view illustrating an example of the set-up for performing the joint operation using the surgical cutting instrument shown in FIG. 1.

The inner tube 5 is provided with a cutting opening 8 for drawing tissue on the outer periphery of the distal end of the inner tube 5 which projects from the distal end of the outer sheath tube 4 and an inner cutting edge 9 is defined on the edge of the cutting opening 8. In addition, the inner tube 5 forms a suction channel 10 for withdrawing cut tissue chips passing through the inner tube communicating with the cutting opening 8 and the proximal end of the inner tube 5 is secured to a stationary member 11 which is fitted into the grip 2. The stationary member 11 has a passage 12 communicating with the suction channel 10 and the passage 12 further communicates with a fitting 13 which is threadably fitted into the stationary member 11 on the outer periphery of the grip 2. The fitting 13, as shown in FIG. 5, communicates with a suction and discharge apparatus 15 through a tube 14 whose one end is connected to the fitting 13 and the other end is connected to the suction and discharge apparatus 15. The cutting opening 8 of the inner tube 5 has a shape as shown in FIGS. 2(A) to 2(D), for example. The cutting opening 8 of FIG. 2(A) is in an axially elongated square shape. The cutting opening 8A of FIG. 2(B) is in a circumferentially extended square form and has the advantage that the extent of projection of the distal end of the inner tube 5 from the distal end of the outer sheath tube 4 can be reduced. The cutting opening 8B of FIG. 2(C) is in a triangular shape whose front side is the base. The cutting opening 8C of FIG. 2(D) is in a triangular shape whose pointed end is the vertex.

Figure 3:
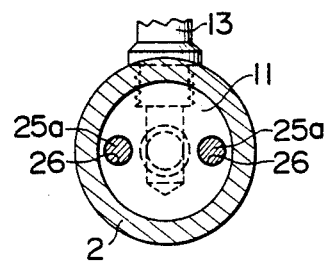
FIG. 3 is a cross-sectional view taken on line III—III in FIG. 1.
Figure 4:
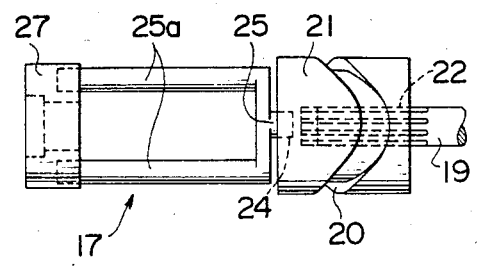
FIG. 4 is a plan view illustrating essential parts of a drive mechanism for a sliding member shown in FIG. 1.

Turning to FIG. 1, the sliding member 7 is formed of a tube the distal end of which is provided with an outer cutting edge 16 which engages the inner cutting edge 9 of the cutting opening 8 and closes the cutting opening 8 when moved forwardly and opens the cutting opening 8 when moved backwardly. The proximal end of the sliding member 7 is inserted into a hollow chamber 2a of the grip 2 and is connected to a drive transmitter 17 which is disposed within the hollow chamber 2a. The drive transmitter 17 includes an output shaft 19 of a drive motor 18 and a cylindrical cam 21 having a circumferentially extended and longitudinally inclined cam groove 20 on the outer periphery of the cam 21. The output shaft 19 and the cam 21 are engaged each other by a spline 19a of the shaft 19 and a spline 22a of the cam 21. In addition, a fixed cam guide pin 23 is fitted into the cam groove 20 so that the cam 21 can be rotatably and slidably moved along the cam groove 21 A slidable shaft 25 is inserted into a rotary center hole 24 provided on the front of the cam 21 to prevent the shaft 25 from coming out and to be rotatably journaled. The slidable shaft 25, as best shown in FIG. 4, has two forked shafts 25a, 25b which respectively pass through through-holes 26, 26 (see FIG. 3) which are axially provided at the right and left positions of the stationary member 11. The distal ends of the forked shafts 25a, 25b are secured to a slidable attachment 27 which is disposed at the proximal end of the inner tube 5 so as to be axially slidable within the hollow chamber 2a. The slidable attachment 27 to which the proximal end of the sliding member 7 is secured is moved back and forth so that the sliding member 7 can be integrally and axially moved with the slidable attachment 27.

The drive motor 18 is electrically connected to a monitor controller 29 (see FIG. 5) through a cable 28 which is extended from the grip 2. The revolution of the motor 18 is controlled by a current, voltage or frequency employing an on-off or a speed controller with an at hand switch provided on the grip 2.

The operation of the surgical cutting instrument 1 of the invention will be explained with reference to FIG. 5. To cut a body region to be excised such as tissue of the knee joint, a small perforation into which the inserter 3 of the instrument 1 is inserted is provided on the knee 30 by a puncture operation as by a trocar. The inserter 3 is then inserted into the joint cavity directly or through a trocar. Prior to the insertion of the inserter 3, an inserter 32 of an arthroscope 31 in which an illumination and observation optical system is disposed is inserted into the joint cavity by a puncture operation as by a trocar so as to permit the cutting operation of tissue to be excised to be effected under observation of the inside of the joint cavity. The inside of the joint cavity and the inserter 3 inserted thereinto can be made observable by an eyepiece of the arthroscope 31 directly or through a display 34 which displays a visual image of a television camera 33 mounted on the eyepiece. Furthermore, to facilitate the cutting operation by inflating the inside of the joint cavity, a physiological solution of sodium chloride is supplied from a solution supplier 35 into the joint cavity with a controlled pressure through a water supply tube 36 which is inserted into the joint cavity. On the other hand, the tube 14 is connected to the fitting 13 on the grip 2 and is further connected to the suction and discharge apparatus 15. A connector (not shown) of the cable 28 is connected to the motor controller 29 to supply a power to the motor 18.

Under these circumstances, an operator takes a step to render the cutting opening 8 bear against tissue to be cut observing the inside of the joint cavity and the distal end of the inserter 3 with an arthroscope or the display 34 to introduce the tissue into the cutting opening 8. Under this condition, a switch is turned on to drive the motor 18. The drive force of the motor 18 actuates the sliding member 7 to axially and slidingly reciprocate it through the drive transmitter 17 so that the outer cutting edge 16 engages the inner cutting edge 9 of the cutting opening 8 to cut or shave the tissue introduced in the cutting opening 8. The tissue chips thus cut are discharged into the suction and discharge apparatus 15 by suction through the suction channel 10, communicating passage 12 of the inner tube 11, fitting 13 and tube 14 activating the suction and discharge apparatus 15 when necessary or normally.

A means for converting the rotary force of the motor to the reciprocating motion to move the sliding member 7 back and forth may be not only the means of the aforesaid embodiment but also one of other various well known means. In addition, in the aforesaid embodiment, the sliding member 7 is illustrated by a tubular body but may be formed with a tubular body merely at the distal end portion of the sliding member 7 on which the outer cutting edge 16 is defined. Alternatively, the sliding member 7 need not be in a tubular shape when it has such width and shape that the distal end portion of the sliding member 7 can close the cutting opening 8. Furthermore, the proximal side of the sliding member 7 may be in any of a tubular, ring and plate shapes.

In the surgical cutting instrument of the invention, the cross sectional form of the inserter 3 may be in any of a circular, elliptic, rectangular and triangular shapes. The sliding member 7 may be reciprocated axially with a manual operation (means for moving the sliding member back and forth by a cruciform handle, a lever or the like). It is to be noted that surgical cutting instrument of the invention can be applied to not only the excising operation of tissue of the joint cavity but also that of another body cavity.

What is claimed is:

1. A surgical cutting instrument comprising:
   an outer sheath tube having an open distal end and a proximal end secured to a grip of the instrument;
   an inner stationary tube having a closed distal end which tube is disposed within said outer sheath tube in such a manner that the distal end of said inner tube projects from said open distal end of said outer sheath tube and its proximal end is secured to said grip;
   a cutting opening provided on the peripheral wall of said projected distal end of the inner tube so as to define a cutting edge on the edge of said cutting opening for drawing cut tissue chips;
   a sliding member which is slidably provided between said outer sheath tube and said inner tube so that the distal end of said sliding member can open and close said cutting opening, said sliding member having an outer cutting edge which engages said inner cutting edge of said cutting opening on the distal end of said sliding member;
   drive means for axially and slidingly reciprocating said sliding member so as to open and close said cutting opening; and
   suction and discharge means connected to said inner tube so as to communicate therewith for effecting the suction operation through a suction channel formed in said inner tube.

2. A surgical cutting instrument according to claim 1, in which said inner stationary tube has a proximal end which is secured to a stationary member which is disposed within said grip so as to communicate with said suction and discharge means through a communicating passage provided within said stationary member and a fitting which is fitted into said stationary member.

3. A surgical cutting instrument according to claim 1, in which said cutting opening is in a rectangular shape elongated in the axial direction of said inner tube.

4. A surgical cutting instrument according to claim 1, in which said cutting opening is in a rectangular shape elongated in the circumferential direction of said inner tube.

5. A surgical cutting instrument according to claim 1, in which said cutting opening is in a triangular shape whose one side is the distal end edge of said inner tube.

6. A surgical cutting instrument according to claim 1, in which said cutting opening is in a triangular shape whose one vertex is at the distal end of said inner tube.

7. A surgical cutting instrument according to claim 1, in which said sliding member which is formed with a tubular body and is disposed between the inner peripheral surface of said outer sheath tube and the outer peripheral surface of said inner tube in a close sliding fit.

8. A surgical cutting instrument according to claim 1, in which said drive means comprises a drive motor, a cylindrical rotatable cam which is connected through a spline mechanism to an output shaft of said motor and is slidingly movable back and forth while rotating through a cam mechanism, a slidable shaft in a forked shape whose proximal end is journaled in said cylindrical cam so as to be axially slidable with the latter while permitting the cylindrical cam to be rotated and a slidable attachment to which said slidable shaft is fixed and which is fixed to the proximal end of said sliding member.

9. A surgical cutting instrument according to claim 8, in which said cam mechanism comprises a cam groove in a spiral form which is provided on the outer peripheral surface of said cylindrical cam and a cam guide pin which is fixedly provided on said grip and is fitted into said cam groove.

10. A surgical cutting instrument according to claim 8, in which said slidable shaft has forked stems passing through through-holes which are provided in said stationary member such that said slidable shaft is prevented from rotating.

* * * * *